United States Patent
Kawamura

(10) Patent No.: US 6,802,200 B2
(45) Date of Patent: Oct. 12, 2004

(54) METHOD FOR INSPECTING THE QUALITY OF A GAS SENSOR, RELATED MANUFACTURING METHOD, AND RELATED INSPECTING APPARATUS

(75) Inventor: Yasushi Kawamura, Yokkaichi (JP)

(73) Assignee: Denso Corporation (JP)

( * ) Notice: Subject to any disclaimer, the term of this patent is extended or adjusted under 35 U.S.C. 154(b) by 105 days.

(21) Appl. No.: 10/107,444

(22) Filed: Mar. 28, 2002

(65) Prior Publication Data

US 2002/0139168 A1 Oct. 3, 2002

(30) Foreign Application Priority Data

Mar. 29, 2001 (JP) ......................................... 2001-096593

(51) Int. Cl.[7] .......................... G01M 3/00; G01M 7/08; G01N 3/30; G01N 3/303
(52) U.S. Cl. ...................... 73/1.06; 73/12.01; 73/12.04; 73/12.06; 73/12.14
(58) Field of Search ............................... 73/1.06, 12.01, 73/12.04, 12.06, 12.09, 12.013, 12.14; 204/401; 29/407.01

(56) References Cited

U.S. PATENT DOCUMENTS

| | | | |
|---|---|---|---|
| 1,223,823 A | | 4/1917 | O'Connor |
| 3,590,631 A | * | 7/1971 | Gonze ............................. 73/94 |
| 3,621,705 A | * | 11/1971 | Antonewick ................ 73/12.01 |
| 4,219,359 A | * | 8/1980 | Miwa et al. ............. 204/415 X |
| 5,355,716 A | | 10/1994 | Castelli ................. 73/12.01 X |
| 5,493,897 A | * | 2/1996 | Nomura et al. ............... 73/23.2 |
| 5,688,390 A | | 11/1997 | Yamauchi et al. .......... 204/426 |
| 5,922,937 A | * | 7/1999 | Kowalski et al. .......... 73/12.14 |
| 2002/0014411 A1 | * | 2/2002 | Shirai .......................... 204/424 |

FOREIGN PATENT DOCUMENTS

| | | | | |
|---|---|---|---|---|
| DE | 3413795 C1 | * | 12/1984 | ................. 73/12.04 |
| DE | 4106929 A1 | * | 9/1992 | ................. 73/12.14 |
| EP | 0 660 101 | | 6/1995 | ............. G01N/3/32 |
| JP | 63-122470 | * | 5/1988 | ................. 73/12.04 |
| JP | 4-282434 | * | 10/1992 | ............. G01N/3/30 |
| JP | 7-140049 | * | 6/1995 | ............. G01M/3/00 |
| JP | 8-193971 | | 7/1996 | ......... G01N/27/405 |

* cited by examiner

Primary Examiner—Thomas P. Noland
(74) Attorney, Agent, or Firm—Nixon & Vanderhye PC

(57) ABSTRACT

An impact force is applied to a sensing element to enlarge the size of a hidden crack to a visible level to reveal the presence of a hidden crack. To apply the impact force to a sensing element, a gas sensor is supported by a holder which is fixed to a distal end of a shaft. The shaft swings about a proximal end thereof serving as a pivot. The holder, with the gas sensor held at its end, is released from a predetermined higher position so as to swing downward about the pivot of the shaft due to gravity. The holder hits a striking plate disposed on a swing path of the holder.

10 Claims, 10 Drawing Sheets

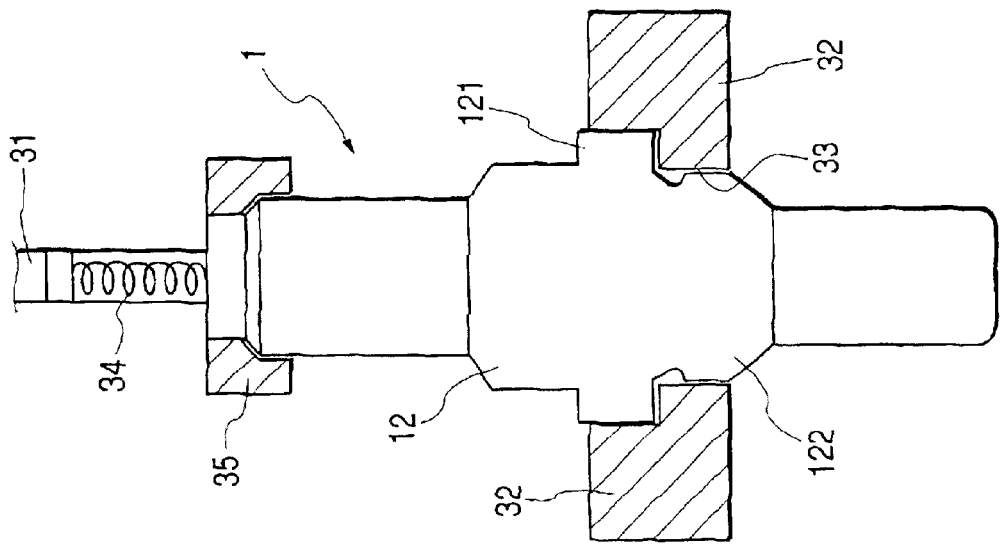
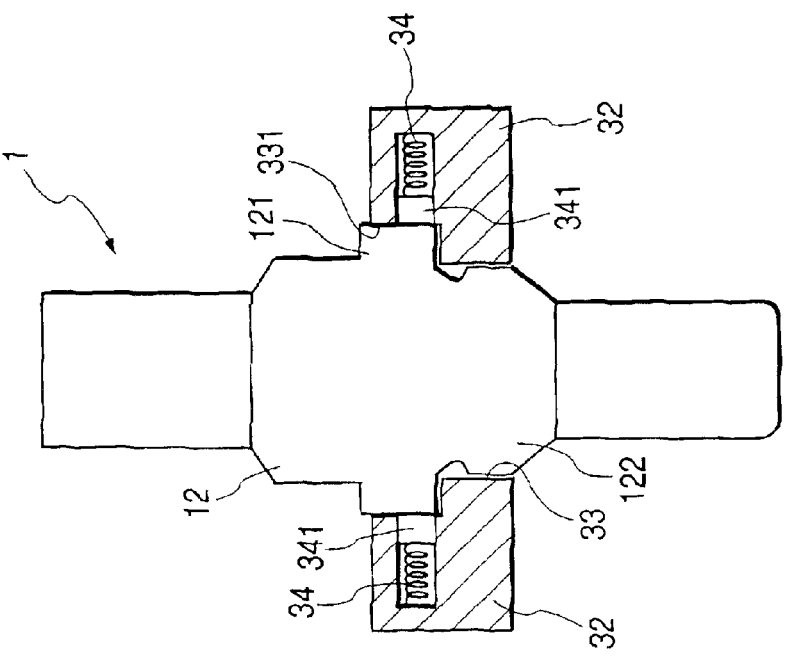
FIG. 8A
FIG. 8B

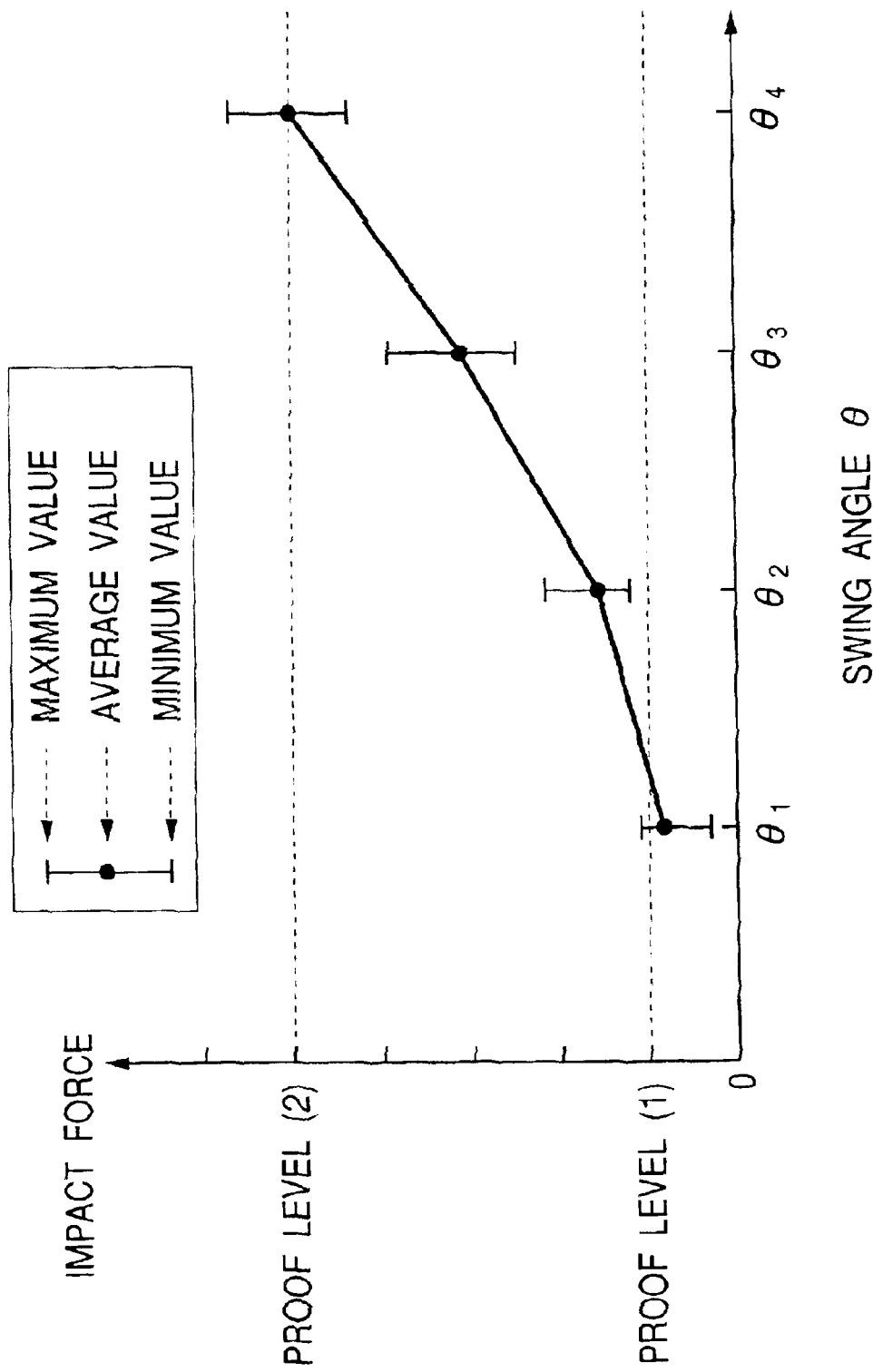

METHOD FOR INSPECTING THE QUALITY OF A GAS SENSOR, RELATED MANUFACTURING METHOD, AND RELATED INSPECTING APPARATUS

BACKGROUND OF THE INVENTION

This invention relates to a method for inspecting the quality of a gas sensor having a sensing element. The present invention also relates to a manufacturing method utilizing the inspecting method of the present invention. Furthermore, the present invention relates to an inspecting apparatus preferably used for performing the inspecting method of the present invention.

Conventionally, the quality inspection for a gas sensor having a sensing element generally includes visual check of the presence of any surficial crack on the sensing element, measurement of gas sensor output characteristics, and check of sensing element airtightness.

However, according to the above-described conventional gas sensor inspection method, it was difficult to find out hidden cracks in a gas sensing element. The hidden cracks include micro cracks or non-through cracks. The gas sensor, if its sensing element has hidden cracks not detectable through the visual inspection, will be judged as non-defective products and will be put into circulation in the market and installed in a practical engine or other device.

The size of such a hidden crack generally increases or grows when the gas sensor is subjected to high-temperature or severe environment during the use of gas sensor. This will possibly lead to the deterioration of gas sensor output characteristics or cause other problems. In other words, the presence of a hidden crack will invite deterioration in the durability of gas sensor.

SUMMARY OF THE INVENTION

In view of the above problems, the present invention has an object to provide a method of inspecting the presence of a hidden crack in a gas sensing element to prevent a defective gas sensor having such an invisible crack in the sensing element from being put into circulation in the market.

Another object of the present invention is to provide a manufacturing method relating to the inspecting method of the present invention.

Furthermore, another object of the present invention is to provide an inspecting apparatus relating to the inspecting method of the present invention.

To accomplish the above and other related objects, the present invention provides a first method for inspecting the quality of a gas sensor having a sensing element characterized in that an impact force is applied to the sensing element to enlarge the size of a hidden crack to a visible level, thereby revealing the presence of the hidden crack.

According to the first inspecting method of the present invention, it becomes possible to change a hidden crack, if involved in the gas sensing element, into a visible and easily detectable crack by applying an impact force. Namely, when the gas sensing element involves a hidden crack, it is generally difficult to find out the hidden crack. However, the first inspecting method of the present invention makes it easy to find out such an invisible crack by forcibly increasing the crack size to a visible level.

Accordingly, if the gas sensing element involves a hidden crack, the first inspecting method of the present invention makes it possible to easily detect such at a defective gas sensing element.

Therefore, the first inspecting method of the present invention prevents a defective gas sensor having an invisible crack in the sensing element from being put into circulation in the market.

As described above, according to the first inspecting method of the present invention, it becomes possible to provide a gas sensor inspecting method capable of preventing a defective gas sensor having an invisible crack in the sensing element from being put into circulation in the market.

The present invention provides a second method for inspecting the quality of a gas sensor having a sensing element disposed in a tubular housing, comprising a step of placing the housing of the gas sensor in a holder which is fixed to a distal end of a shaft, the shaft being swingable on a vertical plane about a proximal end thereof serving as a pivot, and a step of applying an impact force to the sensing element by releasing the holder holding the gas sensor from a predetermined higher position so as to swing downward about the pivot of the shaft due to gravity and then hit a striking plate disposed on a swing path of the holder, thereby applying an impact force to the sensing element. According to the second gas sensor inspecting method of the present invention, the step of applying the impact force to the sensing element is performed plural times from different directions including at least two directions substantially perpendicular to each other with respect to said gas sensor, thereby enlarging the size of a hidden crack to a visible level and revealing the presence of the hidden crack.

According to the second gas sensor inspecting method of the present invention, it becomes possible to provide a gas sensor inspecting method capable of surely preventing a defective gas sensor having an invisible crack in the sensing element from being put into circulation in the market.

The present invention provides a method for manufacturing a gas sensor comprising a step of inserting and fixing a sensing element in a tubular housing and a step of applying an impact force to the sensing element disposed in the housing, thereby confirming that the sensing element includes no visible crack.

According to the manufacturing method of the present invention, it becomes possible to change a hidden crack, if involved in the gas sensing element, into a visible and easily detectable crack by applying an impact force. Namely, when the gas sensing element involves a hidden crack, it is generally difficult to find out the hidden crack. However, the manufacturing method of the present invention makes it easy to find out such an invisible crack by forcibly increasing the crack size to a visible level.

Accordingly, when the gas sensing element involves no visible crack even after the impact force is applied to the gas sensing element, it can be confirmed that the sensing element includes no hidden crack.

According to the manufacturing method of the present invention, it becomes possible to provide a gas sensor manufacturing method capable of obtaining a gas sensor having no invisible crack in the sensing element.

Furthermore, the present invention provides an apparatus for inspecting the quality of a gas sensor. The inspection apparatus of the present invention comprises a holder for holding a sensing element of a gas sensor, a shaft having a proximal end serving as a pivot and a distal end to which the holder is fixed, the shaft being swingable about the pivot so that the sensing element held in the holder can be released from a predetermined higher position, and a striking plate disposed on a swing path of the holder so that an impact force is applied to the sensing element when the sensing element held in the holder is released from the higher position and collides with the striking plate.

According to the inspecting apparatus of the present invention, it becomes possible to simply and accurately perform the quality inspection of a gas sensor.

BRIEF DESCRIPTION OF THE DRAWINGS

The above and other objects, features and advantages of the present invention will become more apparent from the following detailed description which is to be read in conjunction with the accompanying drawings, in which:

FIG. 8A is a cross-sectional view showing a lateral fixing member for fixing the gas sensor coupled in the holder from the side thereof in accordance if with a second embodiment of the present invention;

FIG. 8B is a cross-sectional view showing a vertical fixing means for fixing the gas sensor coupled in the holder from the top thereof in accordance with the second embodiment of the present invention;

FIG. 10 is a graph showing measurement result of the relationship between swing angle θ and obtainable impact force in accordance with the embodiment of the present invention.

DESCRIPTION OF PREFERRED EMBODIMENTS

Figure 1:
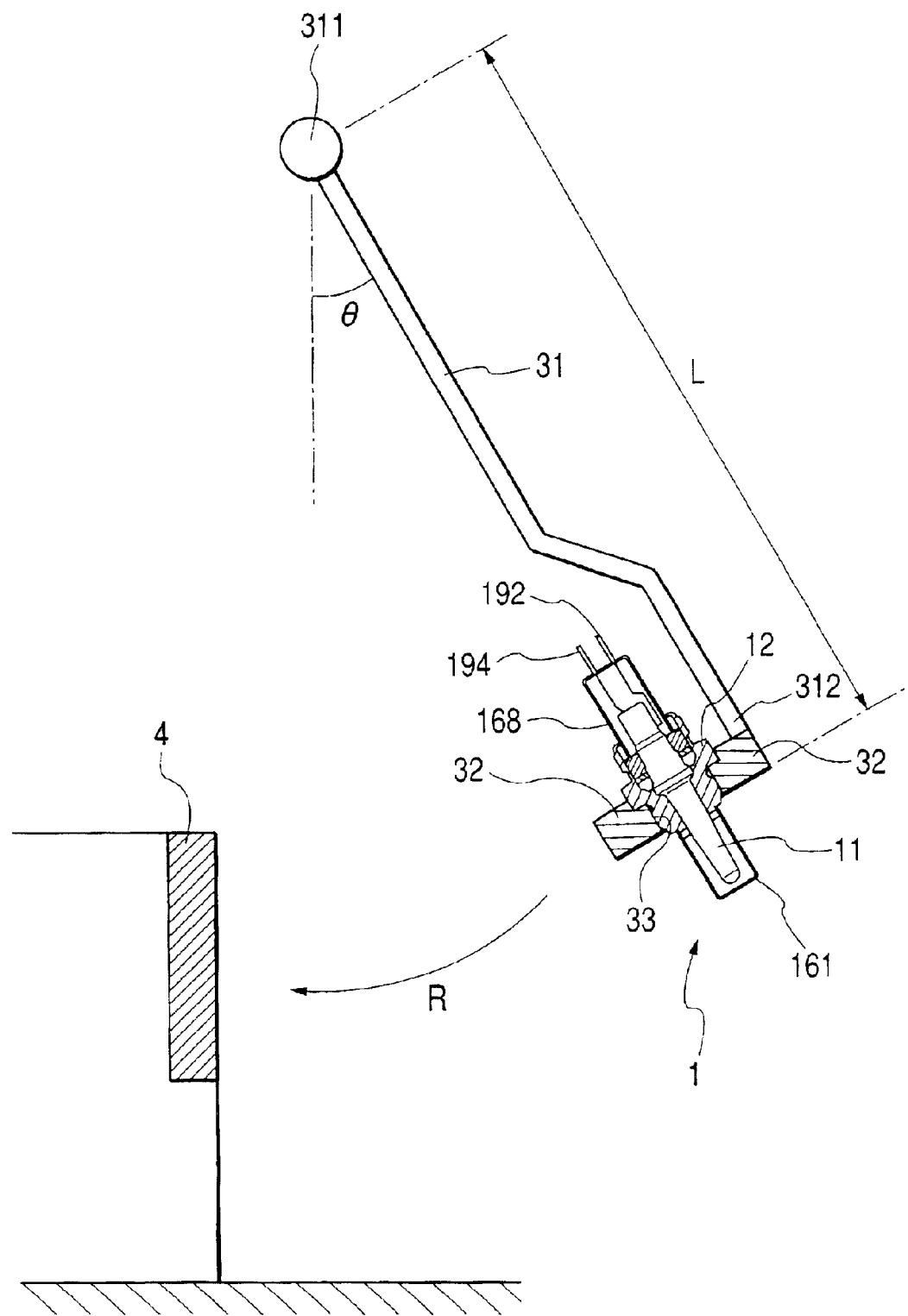
FIG. 1 is a side view showing a gas sensor supported by a holder released from a higher position to apply an impact force to a sensing element of the gas sensor in accordance with a first embodiment of the present invention.

Preferred embodiments of the present invention will be explained hereinafter with reference to attached drawings.

The present invention is applicable for inspecting a gas sensor which measures an oxygen concentration in an exhaust passage to control an air-fuel ratio of an internal combustion engine.

Furthermore, the quality of the gas sensor generally includes strength, durability, and airtightness of a sensing element as well as output characteristics of a gas sensor.

Furthermore, the sensing element is made of for example a ceramic material.

In this description, the 'hidden crack' represents a latent or potential crack which is difficult to find through the visual check. For example, micro cracks and non-through cracks formed in a sensing element are categorized into the hidden cracks. Furthermore, the 'hidden crack' represents a defective crack which may cause a trouble during the use of gas sensor.

On the other hand, the 'visible' crack represents an easily detectable crack. For example, large cracks which are discriminable in size from the hidden cracks are categorized into the visible cracks. Furthermore, full-size cracks which grow and extend entirely across the sensing element are categorized into the visible cracks.

To apply an impact force to the sensing element according to the present invention, it is preferable that the gas sensor is supported by a holder. The holder is fixed to a distal end of a shaft. The shaft is swingable on a vertical plane about a proximal end thereof serving as a pivot. The holder, holding the gas sensor, is released from a predetermined higher position so as to swing downward about the pivot of the shaft due to gravity. And then, the holder hits a striking plate disposed on a swing path of the holder.

According to this arrangement, the impact force can be easily applied to the sensing element. Furthermore, the magnitude of the impact force can be accurately set.

Furthermore, it is preferable that the holder has fixing means for fixing the gas sensor.

With this arrangement, the gas sensor can be securely fixed to the holder. Thus, it becomes possible to apply an accurate impact force to the sensing element.

The impact force of the present invention is applied to the sensing element via the holder. In this respect, the impact force of the present invention is an indirect force. It is preferable to determine the magnitude of the impact force in the following manner.

First, a minimum impact force is determined or designated as lower limit required for surely changing a hidden crack into a visible crack. This lower limit value is referred to as proof level (1). A maximum impact force is determined or designated as upper limit capable of surely preventing an inspected sensing element from causing a new crack if this sensing element has no hidden crack before inspection. This upper limit value is referred to as proof level (2). In other words, when an impact force exceeding the proof level (2) is applied to an inspected sensing element, there is the possibility that a non-defective gas sensor is changed into a defective product through the striking operation. Accordingly, it is preferable that the impact force of the present invention is in the range from the proof level (1) to the proof level (2).

In determining the impact force, its practical value is dependent on the kind of gas sensing element and accordingly can be experimentally determined. The magnitude of the impact force can be expressed in terms of G (i.e., acceleration of gravity).

According to the present invention, it is preferable that the striking operation for applying the impact force to the sensing element is performed plural times for each sensing element.

According to this arrangement, even if the impact force is not so accurate, the hidden crack will be surely changed into the visible crack.

Furthermore, it is preferable that the plural striking operations are performed from different directions with respect to the sensing element.

According to this arrangement, the size of a hidden crack can be surely enlarged into a visible level regardless of the location of hidden crack.

Furthermore, it is preferable that the different directions of the plural striking operations include at least two directions substantially perpendicular to each other with respect to the sensing element.

According to this arrangement, the size of a hidden crack can be surely enlarged into a visible level regardless of the location of hidden crack.

Furthermore, it is preferable that the inspection performed by the present invention includes at least one of output characteristics of the gas sensor and airtightness of the sensing element after finishing the striking operation for applying the impact force to the sensing element.

According to this arrangement, it becomes possible to check the presence of any visible crack on the sensing element based on the output characteristics of the gas sensor and the airtightness of the sensing element. The gas sensor inspection can be easily performed.

Next, it is preferable that the inspection performed by the present invention includes at least one of output characteristics of the gas sensor and airtightness of the sensing element after finishing the striking operation for applying the impact force to the sensing element.

According to this arrangement, it becomes possible to check the presence of any visible crack on the sensing element based on the output characteristics a of the gas sensor and the airtightness of the sensing element. The gas sensor inspection can be easily performed.

Moreover, in applying the impact force to the sensing element in this manufacturing method of the present invention, it is possible to employ the apparatus disclosed in the preferred embodiment of the present invention. It becomes possible to provide a gas sensor manufacturing method capable of surely obtaining a gas sensor free from hidden cracks.

First Embodiment

Figure 4:
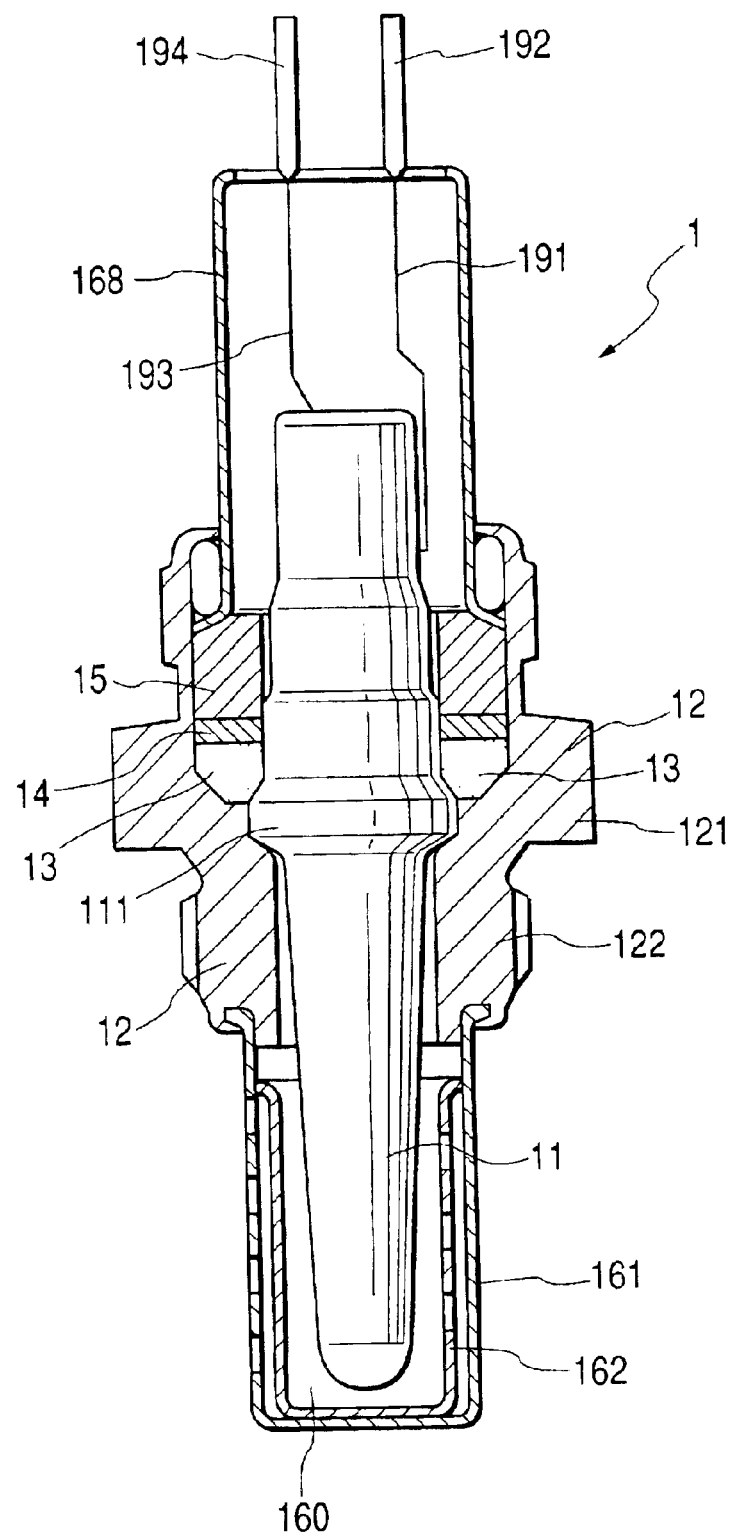
FIG. 4 is a vertical cross-sectional view showing a gas sensor in accordance with the first embodiment of the present invention.
Figure 5A:
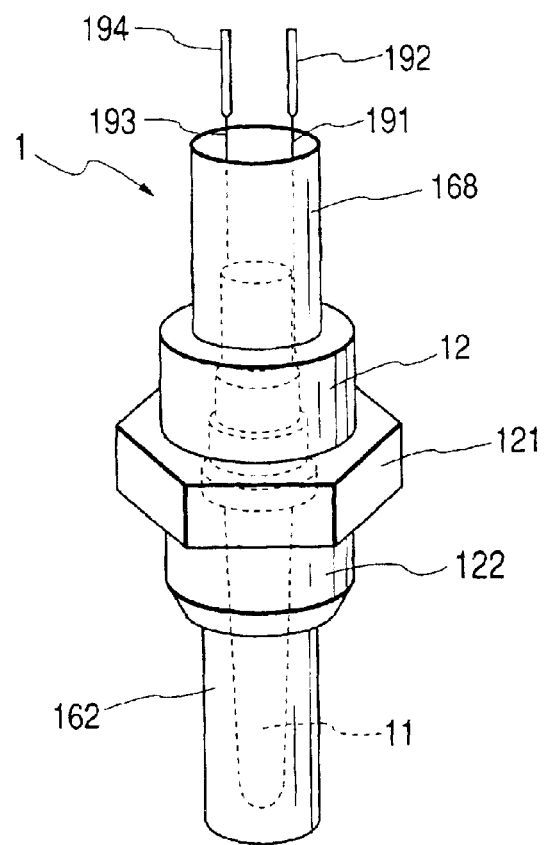
FIG. 5A is a perspective view showing the gas sensor in accordance with the first embodiment of the present invention.

A first embodiment of the present invention relates to a method for inspecting the quality of a gas sensor. FIGS. 4 and 5A show a gas sensor 1 to be inspected. The gas sensor comprises a tubular housing 12. A sensing element 11 is disposed in the housing 12.

Figure 2:
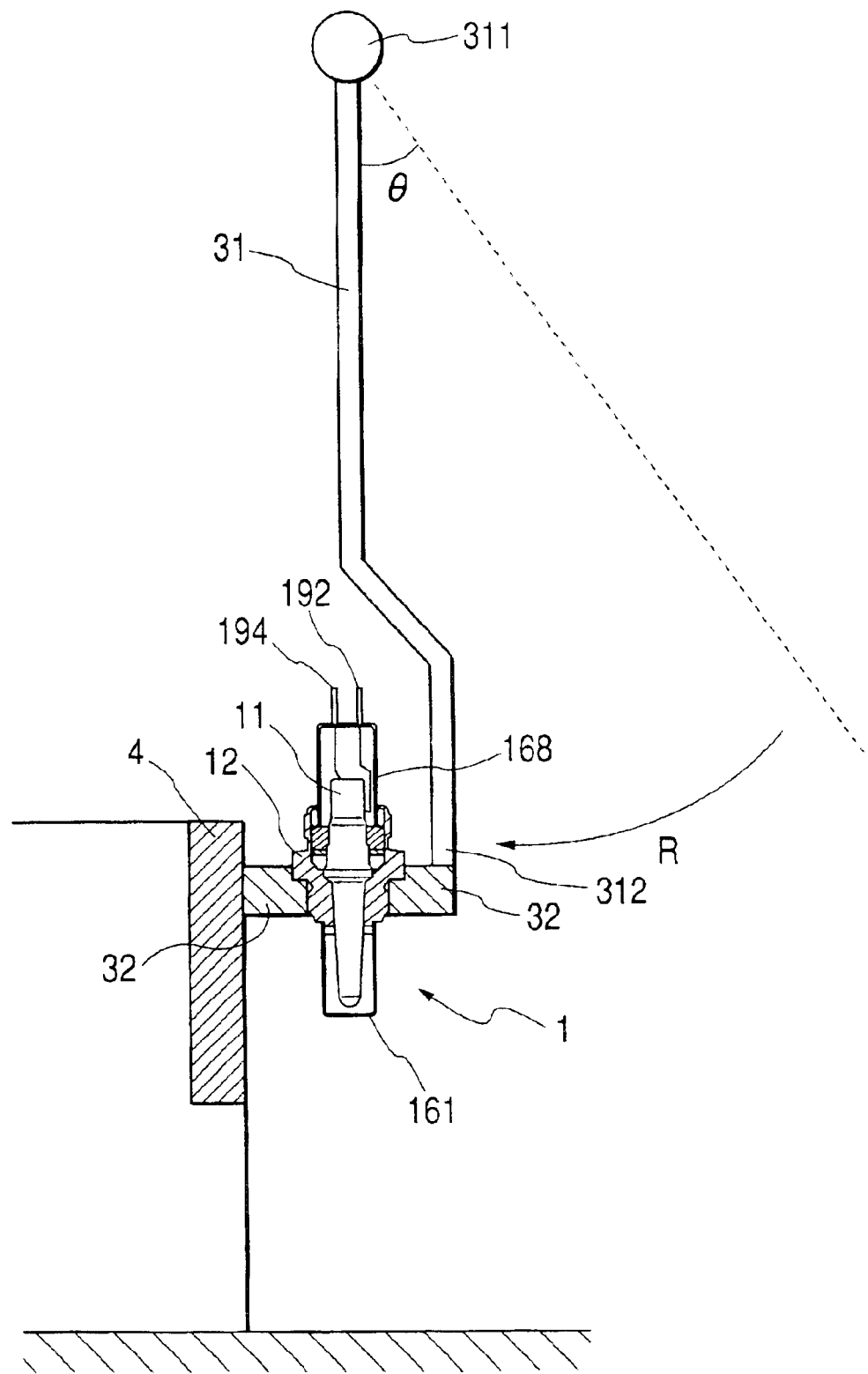
FIG. 2 is a side view showing the moment the holder supporting the gas sensor collides with a striking plate and the impact force is applied to the sensing element.
Figure 3A:
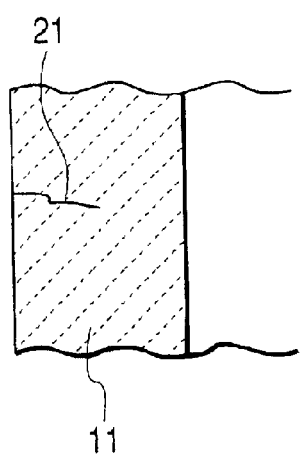
FIG. 3A is a cross-sectional view showing a hidden crack caused in the sensing element of the gas sensor.
Figure 3B:
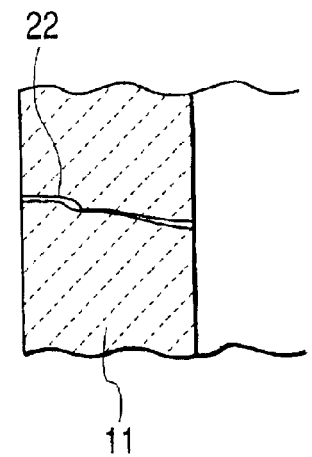
FIG. 3B is a cross-sectional view showing a visible crack forcibly formed by the striking operation applying the impact force to the sensing element (refer to FIGS. 1 and 2) in accordance with first embodiment of the present invention.

FIGS. 1 and 2 are views explaining a striking operation for applying an impact force to the sensing element 11 of the gas sensor 1 in accordance with the inspection method of the first embodiment. When any hidden crack 21 resides in the sensing element 11 (refer to FIG. 3A), the striking operation of this embodiment enlarges the size of hidden crack 21 to a visible size. Namely, the striking operation of this embodiment changes the hidden crack 21 into a visible crack 22 as shown in FIG. 3B.

The gas sensor 1 is used to measure the oxygen concentration in an exhaust passage of an automotive vehicle or any other device to control an air-fuel ratio of an internal combustion engine. The sensing element 11 is made of a ceramic material.

For example, the quality of gas sensor 1 includes strength, durability, and airtightness of sensing element 11 as well as output characteristics of gas sensor 1.

The hidden crack 21 is a latent or potential crack which is difficult to find through the visual check. For example, as shown in FIG. 3A, micro cracks and non-through cracks formed in sensing element 11 are categorized into the hidden cracks 21. Furthermore, the hidden crack 21 is a defective crack which may cause a trouble during the use of gas sensor.

On the other hand, the visible crack 22 is an easily detectable crack. For example, as shown in FIG. 3B, large cracks in size compared with the hidden cracks 21 or full-sized cracks are categorized into the visible cracks 22.

Figure 6:
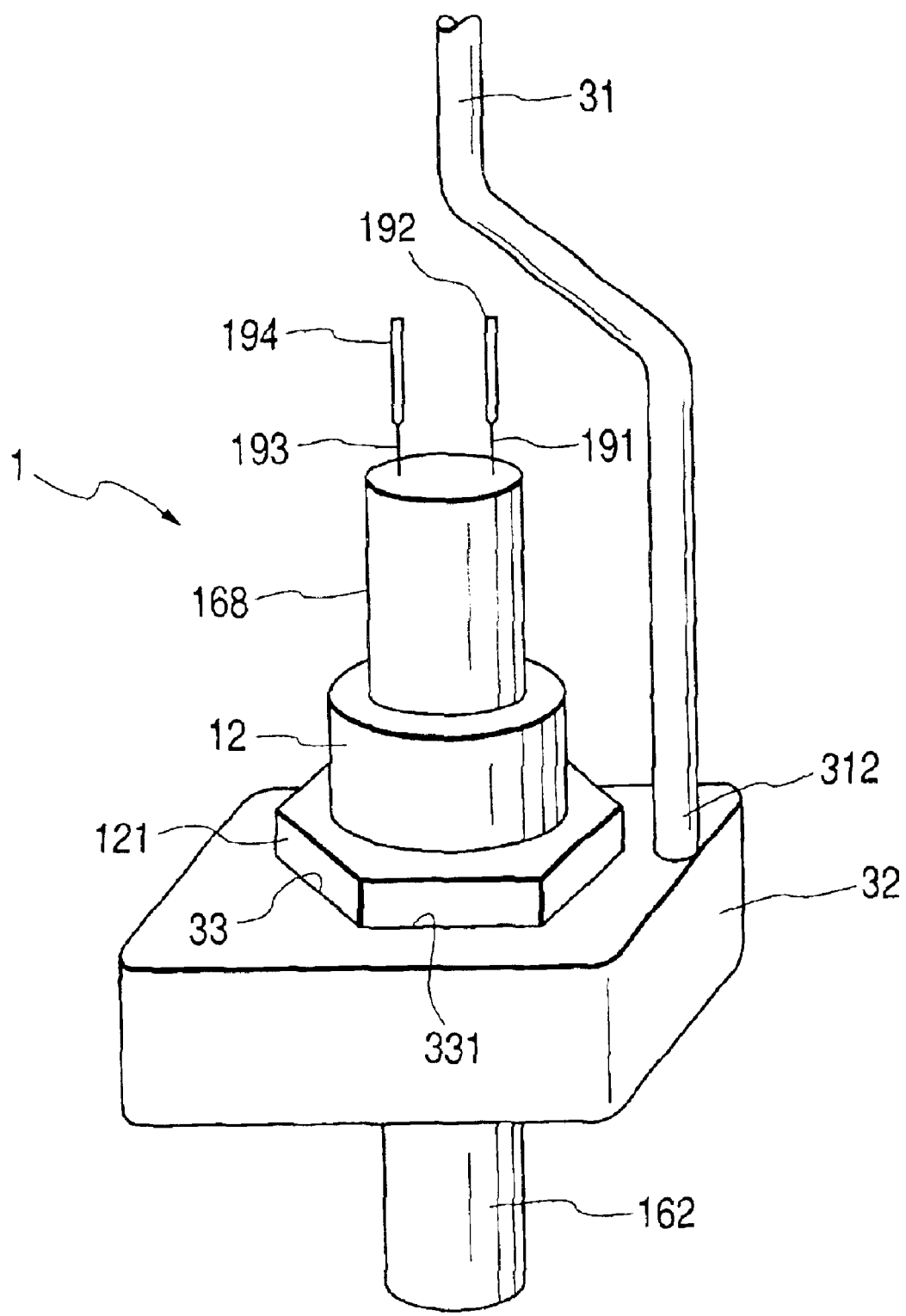
FIG. 6 is a perspective view showing the holder supporting the gas sensor in accordance with the first embodiment of the present invention.

To apply an impact force to the sensing element 11 according to the first embodiment of the present invention, as shown in FIGS. 1, 2 and 6, the housing 12 of gas sensor 1 is supported by a holder 32. The holder 32 is fixed to a distal end 312 of a shaft 31. The shaft 31 is swingable on a vertical plane about a proximal end of shaft 31. In this respect, the proximal end of shaft 31 serves as a pivot 311.

As shown by an arrow R in FIGS. 1 and 2, the holder 32 holding the housing 12 of gas sensor 1 is released from a predetermined higher position. The shaft 31 supporting the holder 32 at its distal end 312 swings downward about the pivot 311 due to gravity. The holder 32 hits a striking plate 4 disposed on a swing path of the holder 32. With this striking operation, an impact force in the range from the proof level (1) to the proof level (2) is applied to the sensing element 11. This impact force enlarges the size of hidden crack 21 to a visible level. As a result, as shown in FIGS. 3A and 3B, the hidden crack 21 residing in the sensing element 11 is forcibly changed into the visible crack 22.

The proof level (1) is a minimum impact force (i.e., lower limit) which is required for surely changing a hidden crack into a visible crack. The proof level (2) is a maximum impact force (i.e., upper limit) capable of surely preventing an inspected sensing element from causing a new crack if this sensing element has no hidden crack before inspection. Accordingly, when the impact force less than 2 the proof level (2) is applied to an inspected sensing element, there is no possibility that a non-defective gas sensor is changed into a defective product through the striking operation.

The striking operation for applying the impact force to the sensing element 11 is performed in the following manner.

First, the distal end 312 of shaft 31 is raised upward about the pivot 311 until a predetermined angle θ is formed with respect to the vertical line passing through the pivot 311 (refer to FIG. 1). Then, the shaft 31 is released. The holder 32 fixed to the distal end 312 of shaft 31 causes a pendular movement due to gravity along a swing path (refer to the arrow R). Then, the holder 32 collides with the striking plate 4 (refer to FIG. 2). The position of striking plate 4 just corresponds to a lowermost point (θ=0) where the distal end 312 of holder 32 can reach.

A dotted line shown in FIG. 2 indicates the initial position of the shaft 31 before the holder 32 is released.

The impact force is dependent on an altitudinal difference between the initial height of holder 32 held at the above-described higher position before the holder 32 is released and the striking height of holder 32 at the moment the holder 32 collides with the striking plate 4. More specifically, the length L of the shaft 31 and the angle θ are decisive factors to evaluate the impact force. The length L is a distance from the pivot 311 to the holder 32.

The gas sensor 1, as shown in FIGS. 4 and 5A, comprises the tubular housing 12 and the sensing element 11 disposed in the housing 12. The sensing element 11 has a flange 111. The flange 111 is brought into contact with an inner wall of the housing 12. A powder 13 is stuffed into an annular end space defined by the flange 111 and the inner wall of the housing 12. A pad 14 and a supporter are successively mounted on the powder 13. A pressing operation is applied to the powder 13 via the pad 14 and the supporter 15.

Double-layered exhaust covers 161 and 162, forming an exhaust gas chamber 160 therein, are attached to a front end of the housing 12.

On the other hand, an atmosphere cover 168 is attached to a rear end of the housing 12. Reference numeral 191 represents a minus lead. Reference numeral 192 represents a minus terminal. Reference numeral 193 represents a plus lead. Reference numeral 194 represents a plus terminal.

The housing 12 has a hexagonal portion 121 protruding radially outward from substantially the center of housing 12. A cylindrical portion 122 is formed adjacent to the hexagonal portion 121 and is offset toward the front end of the housing 12.

Figure 5B:
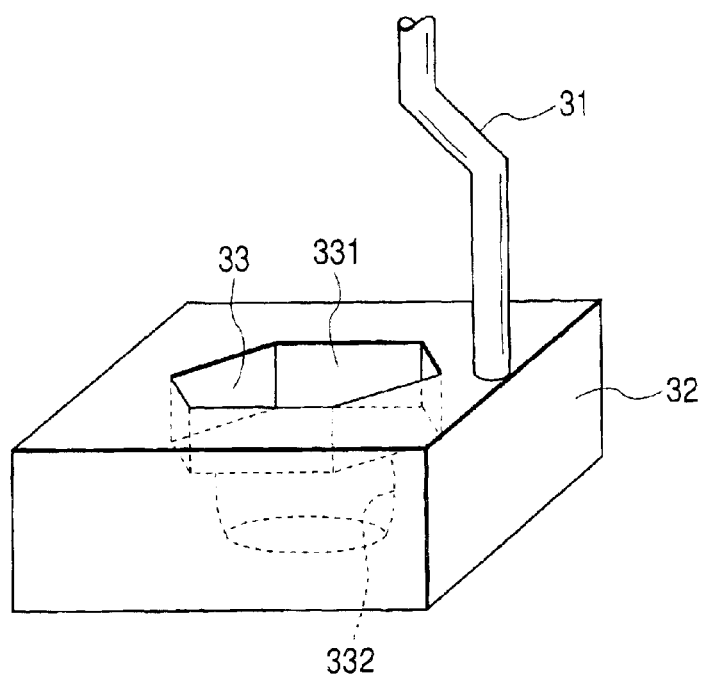
FIG. 5B is a perspective view showing the holder in accordance with the first embodiment of the present invention.

As shown in FIG. 5B, the holder 32 has a receiving hole 33 just coupled with the housing 12 of the gas sensor 1. The receiving hole 33 consists of a hexagonal recess 331 and a circular bore 332 formed next to each other. The hexagonal portion 121 of the housing 12 is just fitted into the hexagonal recess 331 of the receiving hole 33. The cylindrical portion 121 of the housing 12 is just fitted into the circular bore 332 of the receiving hole 33.

The holder 32 and the striking plate 4 are both made of a high-strength carbon steel. The shaft 31 is made of a normal carbon steel.

Figure 7A:
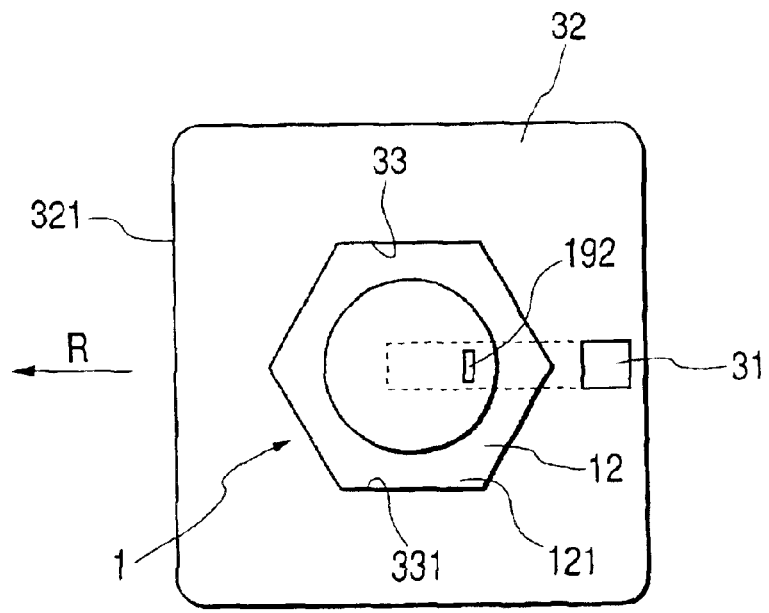
FIG. 7A is a plan view showing the holder supporting the gas sensor held so as to swing in the initial direction for the striking operation in accordance with the first embodiment of the present invention.
Figure 7B:
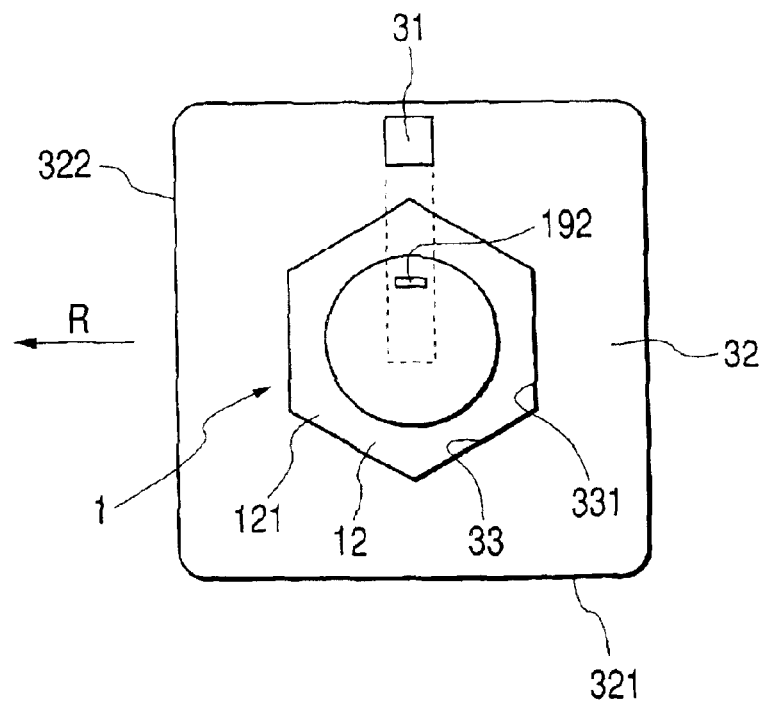
FIG. 7B is a plan view showing the holder supporting the gas sensor held so as to swing in the next direction for the striking operation in accordance with the first embodiment of the present invention.

The striking operation for forcibly colliding the holder 32 against the striking plate 3 is performed plural times from two directions substantially perpendicular to each other with respect to the gas sensor 1, as shown in FIGS. 7A and 7B.

More specifically, one surface 321 of the holder 32 is struck against the striking plate 4 four to six times as shown by the arrow R in FIG. 7A. Then, another surface 322 substantially perpendicular to the surface 321 is struck against the striking plate 4 four to six times as shown by the arrow R in FIG. 7B.

In manufacturing the gas sensor 1 (shown in FIG. 4), the sensing element 11 is inserted into the tubular housing 12 and fixed therein. After the sensing element 11 is securely disposed in the housing 12, an impact force is applied to the sensing element as described above. Through this striking operation, it is checked whether any visible crack 22 is produced in the sensing element 11.

More specifically, the manufacturing of the gas sensor 1 includes a step of attaching the exhaust covers 162 and 161 to the housing 12 and a succeeding step of fixing the attached exhaust covers 162 and 161 by caulking. Next, the sensing element 11 is inserted into the housing 12. Then, the powder 13, the pad 14, and the supporter 15 are successively stuffed into an annular end space defined by the flange 111 of sensing element 11 and the inner wall of housing 12. The powder 13 is pressed by a pressing force applied on the pad 14 and the supporter 15. Then, the atmosphere cover 168 is attached to the housing 12 and is fixed by caulking.

After the gas sensor 1 (shown in FIG. 4) is obtained through the above-described manufacturing processes, an impact force is applied to the sensing element 11. Subsequently, the inspection is performed to check the output characteristics of gas sensor 1 as well as the airtightness of sensing element 11. The gas sensors, when satisfying the required quality level, are shipped as non-defective products.

Next, the functions and effects of the above-described first embodiment will be explained hereinafter.

According to the above-described gas sensor inspecting method of the first embodiment, it becomes possible to change the hidden crack 21, if involved in the sensing element 11, into the visible and easily detectable crack 22. Namely, when the sensing element 11 involves any hidden crack 21, it is generally difficult to find out the hidden crack 21. However, the first embodiment makes it easy to find out such an invisible crack 21 by forcibly increasing the crack size to a visible level.

Accordingly, if the sensing element 11 involves the hidden crack 21, the first embodiment makes it possible to easily detect such a defective sensing element.

Therefore, the present invention prevents a defective gas sensor having the invisible crack 21 in the sensing element 11 from being put into circulation in the market.

To apply an impact force to the sensing element 11, the gas sensor 1 is placed in the holder 32 which is fixed to the distal end 312 of the shaft 31. The holder 32 is released from a predetermined higher position. The holder 32 swings downward about the pivot 311 of the shaft 31 due to gravity and then hits the striking plate 4 disposed on the swing path of the holder 32 (refer to FIGS. 1 and 2). Accordingly, an impact force is easily applied to the sensing element 11. In other words, a desired impact force is accurately applied to the sensing element 11.

Namely, an operator who performs an inspection can easily and accurately apply a desired impact force to the sensing element 11 by adjusting the swing angle θ of the shaft 31.

The impact force is set somewhere in the range from the proof level (1) to the proof level (2). This setting ensures that the hidden crack 21 is surely changed into the visible crack 22 through the striking operation.

Furthermore, the striking operation for applying the impact force to the sensing element 11 is performed plural times for each gas sensor 1. Accordingly, even if the impact force is not so accurate, the hidden crack 21 will be surely changed into the visible crack 22.

Furthermore, the plural striking operations are performed from two directions substantially perpendicular to each other with respect to the sensing element 11. A total of six striking operations are performed from each direction. Accordingly, the size of hidden crack 21 can be surely enlarged into a visible level regardless of the location of hidden crack.

After finishing the striking operation for applying the impact force to the sensing element 11, the inspection is performed to check the output characteristics of gas sensor 1 and the airtightness of sensing element 11. Accordingly, it becomes possible to check the presence of any visible crack 22 on the sensing element 11 based on the output characteristics of gas sensor 1 and the airtightness of sensing element 11. The gas sensor inspection can be easily performed.

In manufacturing the gas sensor 1, the sensing element 11 is fixed to the housing 12 and then an impact force is applied to the sensing element 11 to confirm the presence of visible crack 22.

Accordingly, if any hidden crack 21 resides in the gas sensing element 11, such a hidden crack 21 is changed into a visible and easily detectable crack 22 by applying the impact force. Namely, when the gas sensing element 11 involves a hidden crack 21, it is generally difficult to find out the hidden crack 21. However, this embodiment makes it easy to find out such an invisible crack by forcibly increasing the crack size to the visible level.

Accordingly, when the sensing element 11 involves no visible crack 22 even after the impact force is applied to the sensing element 11, it is confirmed that the sensing element 11 includes no hidden crack 21.

According to this embodiment, it becomes possible to provide the gas sensor 1 having no invisible crack 21 in the sensing element 11.

As described above, this embodiment provides the gas sensor inspecting method and the gas sensor manufacturing method capable of preventing a defective gas sensor having an invisible crack in the sensing element from being put into circulation in the market.

Second Embodiment

A second embodiment of the present invention is characterized in that the holder 32 is provided with a fixing means for fixing gas sensor 1.

For example, as shown in FIG. 8A, the holder 32 is equipped with springs 34. The springs 34 are accommodated in holes extending perpendicularly to the axis of gas sensor 1. The springs 34 are resiliently urged toward the receiving hole 33. A pressing pad 341 is attached to the free end of each spring 34. The pressing pad 341 presses the housing 12 of gas sensor 1 inserted in the receiving hole 33.

With this arrangement, the gas sensor 1 placed in the holder 32 is firmly fixed from the side thereof.

Furthermore, the arrangement of the fixing means can be modified. For example, as shown in FIG. 8B, a pressing jig 35 is disposed just above the holder 32. The pressing jig 35 presses the atmosphere cover 168 from above. The pressing jig 35 is resiliently depressed downward by a spring 34 incorporated in the shaft 31.

With this arrangement, the gas sensor 1 placed in the holder 32 is firmly fixed from the top thereof.

The rest of the second embodiment is substantially identical with that of the first embodiment.

According to the second embodiment, the gas sensor 1 is securely fixed to the holder 32. This makes it possible to accurately apply the impact force to the sensing element 11.

The functions and effects of the second embodiment are similar to those of the first embodiment.

Third Embodiment

A third embodiment of the present invention is characterized in that the shape of holder 32 is modified. As shown in FIGS. 9B and 9C, a holder 320 of the third embodiment has an upper portion 327 having a wider width and a lower portion 328 having a thin width compared with that of the upper portion 327. The upper portion 327 has a side surface 329 which is a combination of a plurality of curved surfaces sequentially arranged in the circumferential direction.

Figure 9A:
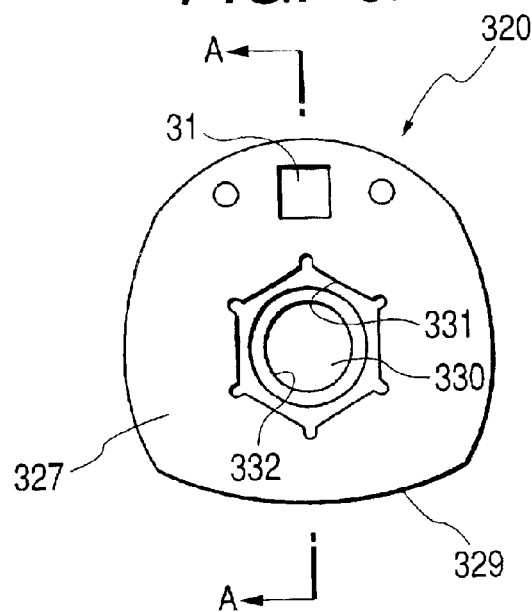
FIG. 9A is a plan view showing a holder in accordance with a third embodiment of the present invention.
Figure 9C:
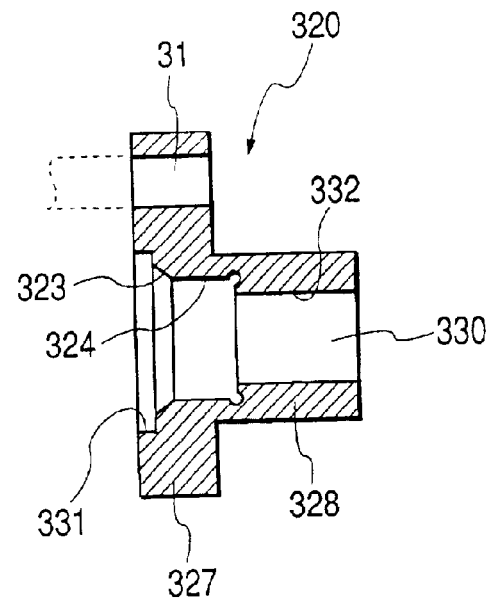
FIG. 9C is a cross-sectional view showing the holder in accordance with the third embodiment of the present invention, taken along a line A—A of FIG. 9A.
Figure 9B:
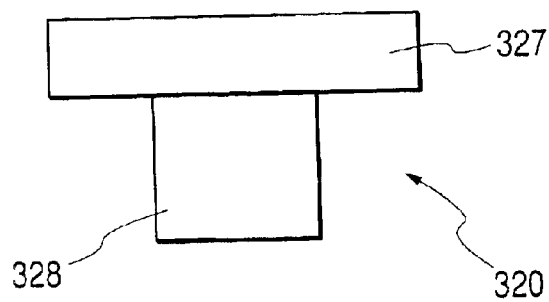
FIG. 9B is a side view showing the holder in accordance with the third embodiment of the present invention.

As shown in FIGS. 9A and 9B, the holder 32 has a receiving hole 330 just coupled with the housing 12 of the gas sensor 1. The receiving hole 330 comprises a hexagonal recess 331 and a circular bore 332 formed integrally via a tapered portion 323 and an intermediate bore 324. The hexagonal recess 331 has a size larger than that of the intermediate bore 324. The tapered portion 323 is formed between the hexagonal recess 331 and the intermediate bore 324. The housing 12 of the gas sensor 1 is smoothly guided by the tapered portion 323 when the gas sensor 1 is coupled in the receiving hole 330 of the holder 320. The intermediate bore 324 has a circular inner wall whose diameter is slightly larger than that of the circular bore 332. The hexagonal portion 121 of the housing 12 is just fitted into the hexagonal recess 331 of the receiving hole 330. The cylindrical portion 121 of the housing 12 is just fitted into the circular bore 332 of the receiving hole 330.

The holder 320 and the striking plate 4 are both made of a high-strength carbon steel. The shaft 31 is made of a normal carbon steel.

The rest of the third embodiment is substantially identical with that of the first embodiment.

According to the third embodiment, it becomes possible to reduce the weight of the holder.

The functions and effects of the third embodiment are similar to those of the first embodiment.

Other than the ones disclosed in the first and third embodiments, the shape as of the holder can be variously modified into an elliptic shape, a circular shape, or any other shape.

FIG. 10 shows the result of a test performed to measure the relationship between the swing angle $\theta$ of holder 32 (refer to FIG. 2) and an obtainable impact force.

In this measurement test, the swing angle $\theta$ of holder 32 was set to four different angles of $\theta 1$, $\theta 2$, $\theta 3$, and $\theta 4$, wherein $\theta 1 < \theta 2 < \theta 3 < \theta 4$. The impact force applied to the sensing element 11 of gas sensor 1 held by the holder 32 was measured for each of the swing angles $\theta 1$, $\theta 2$, $\theta 3$, and $\theta 4$.

To perform this measurement test, the gas sensor 1, the holder 32, and the striking plate 4 or the like disclosed in the first embodiment were used. The length L of shaft 31 used in this measurement test was 540 mm. The measurement of impact force was performed 20 times for each swing angle $\theta$. FIG. 10 shows maximum, minimum, and average values of the impact force obtained in each swing angle $\theta$.

As understood from FIG. 10, when the swing angle $\theta$ is not smaller than $\theta 2$, the obtainable impact force exceeds the proof level (1). Meanwhile, when the swing angle $\theta$ is equal to $\theta 4$, there is the possibility that the obtainable impact force may exceed the proof level (2).

In view of the test result shown in FIG. 10, it is understood that a desirable impact force can be assured when the swing angle $\theta$ is set in the range from $\theta 2$ to $\theta 3$.

This invention may be embodied in several forms without departing from the spirit of essential characteristics thereof. The present embodiments as described are therefore intended to be only illustrative and not restrictive, since on the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for inspecting the quality of a gas sensor having a sensing element, wherein an impact force is applied to said sensing element to enlarge the size of a hidden crack to a visible level so that the presence of said hidden crack is revealed, wherein to apply the impact force to said sensing element, said gas sensor is supported by a holder which is fixed to a distal end of a shaft, said shaft is swingable about a proximal end thereof serving as a pivot, said holder, holding said gas sensor, is released from a predetermined higher position so as to swing downward about said pivot of said shaft due to gravity, and said holder hits a striking plate disposed on a swing path of said holder.

2. The inspecting method for a gas sensor in accordance with claim 1, wherein said holder has fixing means for fixing said gas sensor.

3. The inspecting method for a gas sensor in accordance with claim 1, further comprising a step of inspecting at least one of output characteristics of the gas sensor and airtightness of the sensing element after finishing the step of applying the impact force to said sensing element.

4. The inspecting method for a gas sensor in accordance with claim 1, wherein the impact force applied to said sensing element is in a range from a first proof level to a second proof level, where said first proof level is set as a lower limit required for surely changing the hidden crack into a visible crack, and said second proof level is set as an upper limit capable of surely preventing the impact force from causing a new crack if this sensing element has no hidden crack before inspection.

5. A method for inspecting the quality of a gas sensor having a sensing element, wherein an impact force is applied to said sensing element to enlarge the size of a hidden crack to a visible level so that the presence of said hidden crack is revealed, wherein the striking operation for applying said impact force to said sensing element is performed plural times to said for each sensing element.

6. The inspecting method for a gas sensor in accordance with claim 5, wherein said plural striking operations are performed from different directions with respect to said sensing element.

7. The inspecting method for a gas sensor in accordance with claim 6, wherein said different directions of said plural striking operations include at least two directions substantially perpendicular to each other with respect to the sensing element.

8. A method for inspecting the quality of a gas sensor having a sensing element disposed in a tubular housing, comprising:

a step of placing said housing of the gas sensor in a holder which is fixed to a distal end of a shaft, said shaft being swingable about a proximal end thereof serving as a pivot, and a step of applying an impact force to said sensing element by releasing said holder holding said gas sensor from a predetermined higher position so as to swing downward about said pivot of said shaft due to gravity and then hit a striking plate disposed on a swing path of said holder, thereby applying an impact force to said sensing element, wherein said step of applying the impact force to said sensing element is performed plural times from different directions including at least two directions substantially perpendicular to each other with respect to said gas sensor, thereby enlarging the size of a hidden crack to a visible level and revealing the presence of said hidden crack.

9. The inspecting method for a gas sensor in accordance with claim 8, further comprising a step of inspecting at least one of output characteristics of the gas sensor and airtightness of the sensing element after finishing the step of applying the impact force to said sensing element.

10. The inspecting method for a gas sensor in accordance with claim 8, wherein the impact force applied to said sensing element is in a range from a first proof level to a second proof level, where said first proof level is set as a lower limit required for surely changing the hidden crack into a visible crack, and said second proof level is set as an upper limit capable of surely preventing the impact force from causing a new crack if this sensing element has no hidden crack before inspection.

* * * * *